US007417165B2

(12) United States Patent
Aronhime et al.

(10) Patent No.: US 7,417,165 B2
(45) Date of Patent: Aug. 26, 2008

(54) CRYSTALLINE FORMS OF PREGABALIN

(75) Inventors: Judith Aronhime, Rehovot (IL); Sigalit Levi, Modi'in (IL); Lilach Hedvati, Doar Na Hefer (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/400,484

(22) Filed: Apr. 6, 2006

(65) Prior Publication Data
US 2006/0276543 A1    Dec. 7, 2006

Related U.S. Application Data

(60) Provisional application No. 60/669,131, filed on Apr. 6, 2005.

(51) Int. Cl.
C07C 205/00 (2006.01)
C07C 227/00 (2006.01)
C07B 55/00 (2006.01)

(52) U.S. Cl. ......................... 562/401; 562/553; 562/554

(58) Field of Classification Search ....................... None
See application file for complete search history.

(56) References Cited

U.S. PATENT DOCUMENTS

| | | | |
|---|---|---|---|
| 5,010,189 | A | 4/1991 | Herold et al. |
| 5,599,973 | A | 2/1997 | Silverman et al. |
| 5,616,793 | A | 4/1997 | Huckabee et al. |
| 5,629,447 | A | 5/1997 | Huckabee et al. |
| 5,637,737 | A | 6/1997 | Andres et al. |
| 5,637,767 | A * | 6/1997 | Grote et al. ................. 562/553 |
| 6,197,819 | B1 | 3/2001 | Silverman et al. |
| 6,333,198 | B1 | 12/2001 | Edmeades et al. |
| 6,488,964 | B2 | 12/2002 | Bruna et al. |
| 6,891,059 | B2 | 5/2005 | Burk et al. |
| 6,924,377 | B2 | 8/2005 | Blazecka et al. |
| 7,141,695 | B2 | 11/2006 | Przewosny et al. |
| 2001/0016665 | A1 | 8/2001 | Grote et al. |
| 2003/0225149 | A1 | 12/2003 | Blazecka et al. |
| 2005/0222464 | A1 | 10/2005 | Hoge, II |
| 2005/0228190 | A1 | 10/2005 | Bao et al. |
| 2005/0283023 | A1 | 12/2005 | Hu et al. |
| 2006/0270871 | A1 | 11/2006 | Khanduri et al. |
| 2007/0073085 | A1 | 3/2007 | Hedvati et al. |
| 2008/0014280 | A1 | 1/2008 | Kumar et al. |

FOREIGN PATENT DOCUMENTS

| | | |
|---|---|---|
| CN | 1 634 869 | 7/2005 |
| CZ | 297 970 | 3/2007 |
| WO | WO 96/38405 A1 | 12/1996 |
| WO | WO 96/40617 A1 | 12/1996 |
| WO | WO 01/55090 | 8/2001 |
| WO | WO 2006/000904 A2 | 1/2005 |
| WO | WO 2005/100580 | 10/2005 |
| WO | WO 2006/008640 | 1/2006 |
| WO | WO 2006/136087 | 12/2006 |
| WO | WO 2008/004044 | 1/2008 |
| WO | WO 2008/007145 | 1/2008 |
| WO | WO 2008/009897 | 1/2008 |

OTHER PUBLICATIONS

Andruszkiewicz and Silverman, "A Convenient Synthesis of 3-Alkyl-4-Aminobutanoic Acids," *Synthesis*, 953-955 (1989).
Barnes et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," *J. Am. Chem. Soc.*, 124(44): 13097-13105 (2002).
Berner et al. "Asymmetric Michael Additions to Nitroalkenes," *European Journal of Organic Chemistry*, 1877-1894 (2002).
Cason et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid," *J. Org. Chem.*, 18(9): 1129-1136 (1953).
Chen et al., "Synthesis of Pregabalin," *Zhongguo YiYao Gongye Zazhi*, 35(4): 195-196 (2004).
Colonge et al., "Preparation De Pyrrolidones-2 et de Gamma-Aminoacides," *Bulletin De La Societe Chimique De France, Societe Francaise De Chimie*, 598-603 (1962).
Day and Thorpe, "The Formation and Reactions of Imino-compounds. Part XX. The Condensation of Aldehydes with Cyanoacetamide," *J. Chem. Soc.*, 117: 1465-1474 (1920).
Hoekstra et al., "Chemical Development of CI-1008, an Enantiomerically Pure Anticonvulsant," *Organic Process Research and Development*, 1(1): 26-38 (1997).
Karanewsky et al., "Practical Synthesis of an Enantiomerically Pure Synthon for the Preparation of Mevinic Acid Analogues," *J. Org. Chem.*, 56(11): 3744-3747 (1991).
Li et al., "Highly Enantioselective Catalytic Conjugate Addition of Malonate and β-Ketoester to Nitroalkenes: Asymmetric C-C Bond Formation with New Bifunctional Organic Catalysts Based on Cinchona Alkaloids," *J. Am. Chem. Soc.*, 126(32): 9906-9907 (2004).
Martin et al., "Pregabalin," *Drugs of the Future*, 24(8): 862-870 (1999).
Okino et al., "Enantio- and Diastereoselective Michael Reaction of 1,3-Dicarbonyl Compounds to Nitroolefins Catalyzed by a Bifunctional Thiourea," *J. Am. Chem. Soc.*, 127(1): 119-125 (2005).
Sammis et al., "Highly Enantioselective Catalytic Conjugate Addition of Cyanide to α,β-Unsaturated Imides", *J. Am. Chem. Soc.*, 125(15): 4442-43 (2003).
Shintani et al., "Highly Enantioselective Desymmetrization of Anhydrides by Carbon Nucleophiles: Reactions of Grignard Reagents in the Presence of (−)-Sparteine," *Angewandte Chemie, International Edition*, 41(6): 1057-1059 (2002).

(Continued)

Primary Examiner—Sikarl A Witherspoon
(74) Attorney, Agent, or Firm—Kenyon & Kenyon LLP

(57)    ABSTRACT

Crystalline form of Pregabalin characterized by X-ray powder diffraction peaks at about 5.8, 18.4, 19.2, 20.7, and 23.7° 2θ±0.2° 2θ, methods for its preparation, its pharmaceutical compositions thereof, and methods for the preparation of crystalline form of Pregabalin characterized by X-ray powder diffraction peaks at about 5.7, 15.4, 17.2, 18.2, and 23.0° 2θ±0.2° 2θ, are provided.

21 Claims, 2 Drawing Sheets

OTHER PUBLICATIONS

Snyder et al., Introduction to Modern Liquid Chromatography, 549-572 (2d ed., John Wiley & Sons, 1979).

Strobel et al., Chemical Instrumentation: A Systematic Approach, 391-393, 879-894, 922-925, 953 (3d ed. 1989).

Theisen et al., "Prochiral Recognition in the Reaction of 3-Substituted Glutaric Anhydrides with Chiral Secondary Alcohols," *J. Org. Chem.*, 58(1): 142-146 (1993).

Verma et al., "Desymmetrization of prochiral anhydrides with Evans' oxazolidinones: an efficient route to homochiral glutaric and adipic acid derivatives," *J. Chem. Soc., Perkin Transactions 1: Organic and Bio-Organic Chemistry*, 257-264 (1999).

Yamamoto et al., "Stereoselective Synthesis of (E)-Alkylidenesuccinates by Palladium-catalyzed Carbonylation," *Bull. Chem. Soc. Japan*, 58(11): 3397-3398 (1985).

* cited by examiner

Figure 1. X-Ray powder diffractogram of a crystalline form of Pregabalin characterized by X-ray powder diffraction peaks at about 5.8, 18.4, 19.2, 20.7, and 23.7° $2\theta \pm 0.2°$ $2\theta$.
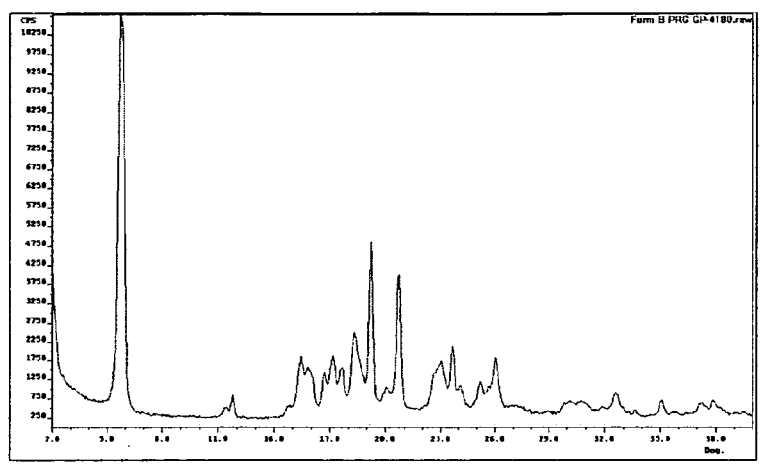
Figure 2. TGA thermogram of a crystalline form of Pregabalin characterized by X-ray powder diffraction peaks at about 5.8, 18.4, 19.2, 20.7, and 23.7° $2\theta \pm 0.2°$ $2\theta$.
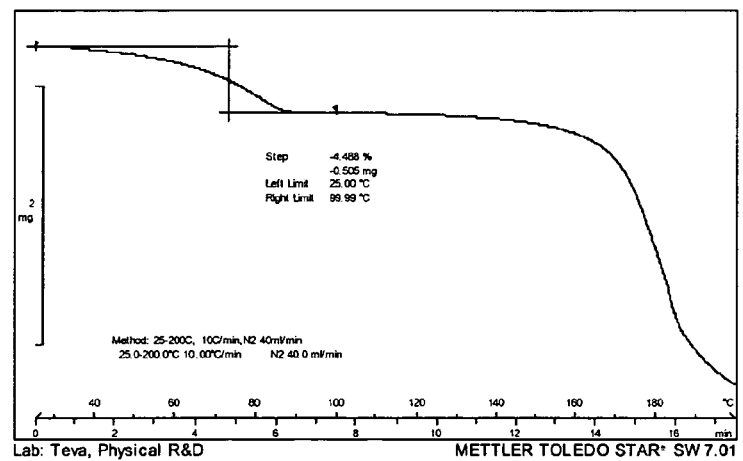

Figure 3. DSC thermogram of a crystalline form of Pregabalin characterized by X-ray powder diffraction peaks at about 5.8, 18.4, 19.2, 20.7, and 23.7° 2θ ± 0.2° 2θ.
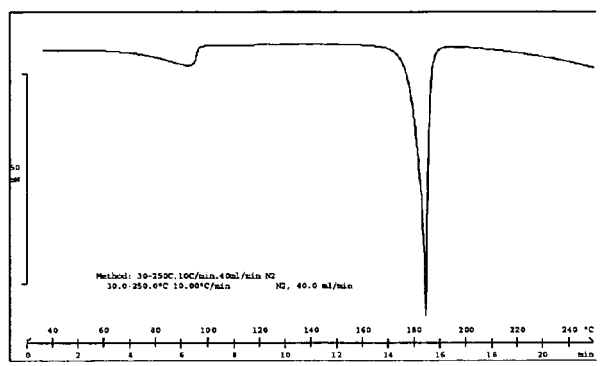
Figure 4. X-Ray powder diffractogram of Pregabalin crystalline form characterized by X-ray powder diffraction peaks at about 5.7, 15.4, 17.2, 18.2, and 23.0° 2θ ± 0.2° 2θ according to example 2.
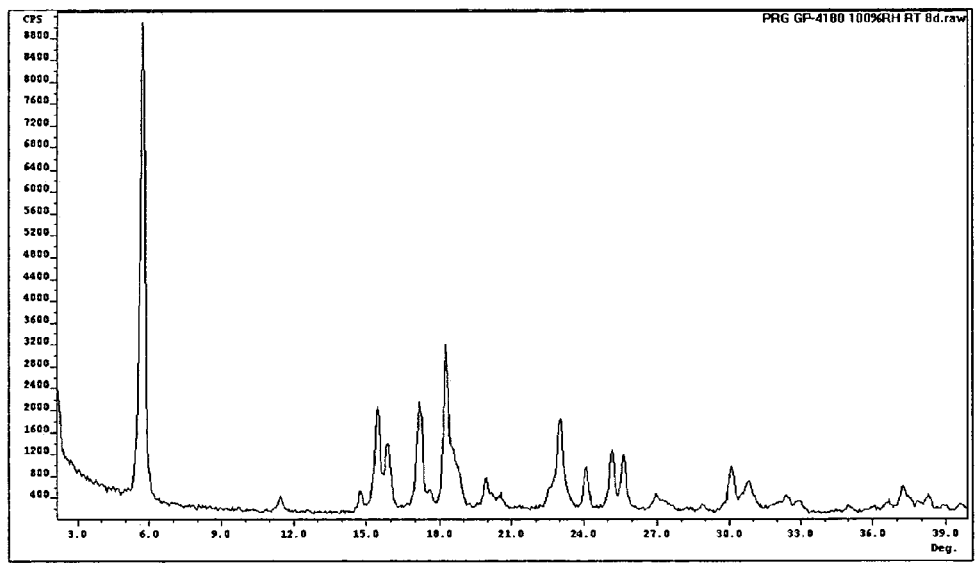

CRYSTALLINE FORMS OF PREGABALIN

RELATED APPLICATION

This application claims benefit of U.S. Provisional Patent Application No. 60/669,131, filed Apr. 6, 2005, the contents of which are incorporated herein in their entirety by reference.

FIELD OF THE INVENTION

The present invention is directed to novel crystalline form of Pregabalin, methods for its preparation, and pharmaceutical compositions thereof.

BACKGROUND OF THE INVENTION (S)-Pregabalin, (S)-(+)-3-(aminomethyl)-5-methylhexanoic acid, a compound having the chemical structure,

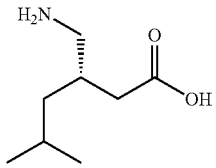

is also known as γ-amino butyric acid or (S)-3-isobutyl GABA. (S)-Pregabalin, marketed under the name LYRICA®, has been found to activate GAD (L-glutamic acid decarboxylase). (S)-Pregabalin has a dose dependent protective effect on-seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity.

U.S. Pat. No. 5,637,767 discloses crystalline racemic pregabalin which is a monohydrate.

The present invention relates to the solid state physical properties of Pregabalin. These properties can be influenced by controlling the conditions under which Pregabalin is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetric (DSC) and can be used to distinguish some polymorphic forms from others. A particular polymorphic form may also give rise to distinct spectroscopic properties that may be detectable by powder X-ray crystallography, solid state $^{13}C$ NMR spectrometry, and infrared spectrometry.

The present invention also relates to solvate of Pregabalin. When a substance crystallizes out of solution, it may trap molecules of solvent at regular intervals in the crystal lattice. Solvation also affects utilitarian physical properties of the solid state like flowability and dissolution rate.

One of the most important physical properties of a pharmaceutical compound, which can form polymorphs or solvates, is its solubility in aqueous solution, particularly the solubility in gastric juices of a patient. Other important properties relate to the ease of processing the form into pharmaceutical dosages, as the tendency of a powdered or granulated form to flow and the surface properties that determine whether crystals of the form will adhere to each other when compacted into a tablet.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

SUMMARY OF THE INVENTION

The present invention encompasses crystalline Pregabalin hemihydrate.

The present invention further encompasses a crystalline form of Pregabalin characterized by X-ray powder diffraction peaks at about 5.8, 18.4, 19.2, 20.7, and 23.7° 2θ±0.2° 2θ.

The present invention encompasses pharmaceutical formulations comprising any of the crystalline forms of Pregabalin of the present invention, and pharmaceutically acceptable excipient.

The present invention further encompasses a process for preparing a pharmaceutical formulation comprising combining any of the crystalline forms of Pregabalin of the present invention with at least one pharmaceutically acceptable excipient.

The present invention further encompasses the use of the crystalline form of Pregabalin of the present invention for the manufacture of a pharmaceutical composition.

The present invention encompasses a process of preparing Pregabalin characterized by X-ray powder diffraction peaks at about 5.7, 15.4, 17.2, 18.2, and 23.0° 2θ±0.2° 2θ by exposing Pregabalin characterized by X-ray powder diffraction peaks at about 5.8, 18.4, 19.2, 20.7, and 23.7° 2θ±0.2° 2θ to a relative humidity of about 80 to about 100 percent, at about room temperature for at least about a week.

BRIEF DESCRIPTION OF THE DRAWINGS

FIG. 1. X-Ray powder diffractogram of Pregabalin crystalline form characterized by X-ray powder diffraction peaks at about 5.8, 18.4, 19.2, 20.7, and 23.7° 2θ±0.2° 2θ.

FIG. 2. TGA thermogram of Pregabalin crystalline form characterized by X-ray powder diffraction peaks at about 5.8, 18.4, 19.2, 20.7, and 23.7° 2θ±0.2° 2θ.

FIG. 3. DSC thermogram of Pregabalin crystalline form characterized by X-ray powder diffraction peaks at about 5.8, 18.4, 19.2, 20.7, and 23.7° 2θ±0.2° 2θ.

FIG. 4. X-Ray powder diffractogram of Pregabalin crystalline form characterized by X-ray powder diffraction peaks at about 5.7, 15.4, 17.2, 18.2, and 23.0° 2θ±0.2° 2θ according to example 2.

DETAILED DESCRIPTION OF THE INVENTION

As used herein, the term "Pregabalin" refers to pregabalin racemate.

The present invention encompasses crystalline Pregabalin hemihydrate.

The present invention further encompasses a crystalline form of Pregabalin characterized by X-ray powder diffraction peaks at about 5.8, 18.4, 19.2, 20.7, and 23.7° 2θ±0.2° 2θ. The crystalline form may be further characterized by X-ray powder diffraction peaks at about 15.5, 17.2, 23.0, and 26.0° 2θ±0.2° 2θ. The crystalline form may be also substantially identified by the PXRD pattern depicted in FIG. 1.

The above crystalline form may be further characterized by a DSC thermogram with a broad endotherm at about 60° C. to about 100° C. and another endothermic peak at 181° C. Also, the crystalline form may be substantially identified by the DSC curve depicted in FIG. 3. In addition, the crystalline form may be further characterized by TGA showing a weight loss of about of 4.5 percent up to about 100° C. Moreover, the crystalline form may be substantially identified by the TGA curve depicted in FIG. 2. The above crystalline form may be a hemihydrate form of Pregabalin; preferably, having a Karl-Fisher water content of about 5.3 percent by weight. The crystalline form of Pregabalin characterized by X-ray powder diffraction peaks at about 5.8, 18.4, 19.2, 20.7, and 23.7° 2θ±0.2° 2θ may have a melting point of about 162° C. to about 165° C. Preferably, the above crystalline form has an average particle size that is smaller than about 300 microns. Preferably, the above crystalline form is polymorphically pure, i.e., contains no more than about 10% of other forms, such as the crystalline form of Pregabalin characterized by X-ray powder diffraction peaks at about 5.7, 15.4, 17.2, 18.2, and 23.0° 2θ±0.2° 2θ. More preferably, the above crystalline form contains no more than about 5% of other forms, such as the crystalline form of Pregabalin characterized by X-ray powder diffraction peaks at about 5.7, 15.4, 17.2, 18.2, and 23.0° 2θ±0.2° 2θ.

The invention also encompasses a process of preparing a crystalline form of Pregabalin characterized by X-ray powder diffraction peaks at about 5.8, 18.4, 19.2, 20.7, and 23.7° 2θ±0.2° 2θ by crystallization from a mixture of acetonitrile and an alcohol. The process comprises dissolving Pregabalin in a mixture of acetonitrile and an alcohol, heating, and cooling to obtain a precipitate. The mixture is then, preferably, filtered, and the collected solid is dried. Preferably, the Pregabalin used as a starting material is Pregabalin crystalline form characterized by X-ray powder diffraction peaks at about 5.7, 15.4, 17.2, 18.2, and 23.0° 2θ±0.2° 2θ. Preferably, the alcohol is $C_3$-$C_9$ alcohol. More preferably, the alcohol is n-butanol. Preferably, the heating is done to a temperature of about 40° C. to about 100° C. More preferably, the heating is done to a temperature of about 45° C. to about 55° C. Most preferably, the heating is done at a temperature of about 50° C. Preferably, the heating is done for at least about an hour. More preferably, the heating is done for about 2 hours. Preferably, the cooling is done to a temperature of about 2° C. to about 15° C. More preferably, the cooling is done to a temperature of about 10° C. over a period of several hours. Preferably, the cooling is for about 8 hours.

Another aspect of the present invention provides a process of preparing a crystalline form of Pregabalin characterized by X-ray powder diffraction peaks at about 5.8, 18.4, 19.2, 20.7, and 23.7° 2θ±0.2° 2θ by heating a crystalline form of Pregabalin characterized by X-ray powder diffraction peaks at about 5.7, 15.4, 17.2, 18.2, and 23.0° 2θ±0.2° 2θ at a temperature of at least about 100° C., for at least about 30 minutes. Preferably, the heating is done to a temperature of about 100° C. to about 130° C., more preferably, to a temperature of about 120° C. Preferably, the heating is done for about 30 minutes to about 2 hours, more preferably, for about one hour.

The crystalline form of Pregabalin characterized by X-ray powder diffraction peaks at about 5.7, 15.4, 17.2, 18.2, and 23.0° 2θ±0.2° 2θ may be prepared, for example, according to the process disclosed in U.S. Pat. No. 5,637,767.

The present invention encompasses a process of preparing Pregabalin characterized by X-ray powder diffraction peaks at about 5.7, 15.4, 17.2, 18.2, and 23.0° 2θ±0.2° 2θ by exposing Pregabalin characterized by X-ray powder diffraction peaks at about 5.8, 18.4, 19.2, 20.7, and 23.7° 2θ±0.2° 2θ to a relative humidity of about 80 to about 100 percent, at about room temperature for at least about a week. Preferably, the relative humidity is of about 100 percent.

The crystalline forms of the present invention may be converted to S-pregabalin, for example, by the method described in U.S. Pat. No. 5,637,767.

The present invention also encompasses pharmaceutical formulations comprising any of the crystalline forms of Pregabalin of the present invention, and pharmaceutically acceptable excipient.

The present invention further encompasses a process for preparing a pharmaceutical formulation comprising combining any of the crystalline forms of Pregabalin of the present invention with at least one pharmaceutically acceptable excipient.

The present invention further encompasses the use of the crystalline form of Pregabalin of the present invention for the manufacture of a pharmaceutical composition.

Methods of administration of a pharmaceutical composition of the present invention can be administered in various preparations depending on the age, sex, and symptoms of the patient. The pharmaceutical compositions can be administered, for example, as tablets, pills, powders, liquids, suspensions, emulsions, granules, capsules, suppositories, injection preparations (solutions and suspensions), and the like.

Pharmaceutical compositions of the present invention can optionally be mixed with other forms of Pregabalin and/or other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. AVICEL®, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, pregabalin and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

When preparing injectable (parenteral) pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

EXPERIMENTAL

The X-Ray powder diffraction data were obtained using methods known in the art, using a SCINTAG powder X-Ray diffractometer model X'TRA equipped with a solid-state detector, copper radiation of 1.5418 Å, and a round aluminum sample holder with zero background. All peak positions were within ±0.2° 2θ. The scanning parameters included: range: 2° to 40° 2θ; scan mode: continuous scan; step size: 0.050; and a rate of 5°/min.

The DSC analysis was performed using a Mettler 821 Stare. The weight of the samples was about 5 mg. The samples were scanned at a rate of 10° C./min from about 30° C. to about 250° C. The oven was constantly purged with nitrogen gas at a flow rate of about 40 ml/min. Standard 40 ml aluminum crucibles covered by lids with three holes were used.

The TGA analysis was done using a Mettler M3 thermogravimeter. The weight of the samples was about 8 mg; the samples were scanned at a rate of 10° C./min from about 25° C. to about 200° C. A blank was subtracted from the sample. The oven was constantly purged with nitrogen gas at a flow rate of about 40 ml/min. Standard 150 μl alumina crucibles covered by lids with 1 hole were used.

EXAMPLE 1

Comparative Example According to U.S. Pat. No. 5,637,767: Preparation of a Crystalline Form of Pregabalin Characterized by X-ray Powder Diffraction Peaks at about 5.7, 15.4, 17.2, 18.2, and 23.0° 2θ±0.2° 2θ

First, 400 g of crude Pregabalin was charged into a round bottom flask containing 2.8 l of a 14 percent aqueous isopropyl alcohol solution. The mixture was heated to reflux for about 50 to about 60 min. After cooling to about 0° to about 5° C., and stirring for about 60 to about 90 min, the mixture was filtered. The solid was washed with 400 ml of a 14 percent aqueous isopropyl alcohol solution, and dried under vacuum at about 55° to about 60° C. until a constant weight was achieved.

EXAMPLE 2

Preparation of a Crystalline Form of Pregabalin Characterized by X-ray Powder Diffraction Peaks at about 5.7, 15.4, 17.2, 18.2, and 23.0° 2θ±0.2° 2θ

A crystalline form of Pregabalin characterized by X-ray powder diffraction peaks at about 5.7, 15.4, 17.2, 18.2, and 23.0° 2θ+0.2° 2θ was prepared by exposing a crystalline form of Pregabalin characterized by X-ray powder diffraction peaks at about 5.8, 18.4, 19.2, 20.7, and 23.7° 2θ±0.2° 2θ to a relative humidity of about 100 percent at about room temperature for about 8 days. The melting point of the crystalline form was also determined, and found to be between 162° and 165° C.

EXAMPLE 3

Preparation of a Crystalline Form of Pregabalin Characterized by X-ray Powder Diffraction Peaks at about 5.8, 18.4, 19.2, 20.7, and 23.7° 2θ±0.2° 2θ by Crystallization 0.5 g of a crystalline form of Pregabalin characterized by X-ray powder diffraction peaks at about 5.7, 15.4, 17.2, 18.2, and 23.0° 2θ±0.2° 2θ was charged into round bottom flask containing 54 ml of n-butanol and 27 ml of acetonitrile. The mixture was heated to 50° C. for about 2 hours, and cooled to about 10° C. over a period of about 8 hours. The mixture was then filtered, and the solid was dried at 45° C. under a 10 vacuum of mm Hg.

EXAMPLE 5

Preparation of a Crystalline Form of Pregabalin Characterized by X-ray Powder Diffraction Peaks at about 5.8, 18.4, 19.2, 20.7, and 23.7° 2θ±0.2° 2θ by Drying 200 mg of a crystalline form of Pregabalin characterized by X-ray powder diffraction peaks at about 5.7, 15.4, 17.2, 18.2, and 23.0° 2θ±0.2° 2θ was placed in oven at 120° C. for one hour. The heated sample was analyzed by XRD, and found to be a crystalline form of Pregabalin characterized by X-ray powder diffraction peaks at about 5.8, 18.4, 19.2, 20.7, and 23.7° 2θ±0.2° 2θ. The melting point of the crystalline form was determined, and found to be 165° C.

What is claimed is:

1. A process of preparing crystalline pregabalin characterized by X-ray powder diffraction peaks at about 5.8, 18.4, 19.2, 20.7, and 23.7° 2θ±0.2° 2θ, comprising crystallizing the crystalline pregabalin from a mixture of acetonitrile and an alcohol.

2. The process of claim 1, wherein the crystallization comprises dissolving pregabalin in the mixture of acetonitrile and an alcohol to form a solution, heating the solution, and cooling the solution to obtain a precipitate of the crystalline pregabalin characterized by X-ray powder diffraction peaks at about 5.8, 18.4, 19.2, 20.7, and 23.7° 2θ±0.2° 2θ.

3. The process of claim 2, wherein the pregabalin that is dissolved in the mixture of acetonitrile and an alcohol is crystalline pregabalin characterized by X-ray powder diffraction peaks at about 5.7, 15.4, 15.9, 17.2, 18.2, 18.5, 23.0, 25.2, and 25.6° 2θ±0.2° 2θ.

4. The process of claim 2, wherein the alcohol is a $C_3$-$C_9$ alcohol.

5. The process of claim 4, wherein the alcohol is n-butanol.

6. The process of claim 2, wherein the solution is heated to a temperature of about 40° to about 100° C.

7. The process of claim 6, wherein the solution is heated to a temperature of about 45° to about 55° C.

8. The process of claim 7, wherein the solution is heated to a temperature of about 50° C.

9. The process of claim 2, wherein the solution is heated for at least about an hour.

10. The process of claim 9, wherein the solution is heated for about 2 hours.

11. The process of claim 2, wherein the solution is cooled to a temperature of about 2° C. to about 15° C.

12. The process of claim 11, wherein the solution is cooled to a temperature of about 10° C.

13. The process of claim 2, wherein the solution is cooled for about 8 hours.

14. The process of claim 2, further comprising filtering the precipitate from the solution and drying the precipitate.

15. A process of preparing crystalline pregabalin characterized by X-ray powder diffraction peaks at about 5.8, 18.4, 19.2, 20.7, and 23.7° 2θ±0.2° 2θ comprising heating crystalline pregabalin characterized by X-ray powder diffraction peaks at about 5.7, 15.4, 15.9, 17.2, 18.2, 18.5, 23.0, 25.2, and 25.6° 2θ±0.2° 2θ at a temperature of at least about 100° C., for at least about 30 minutes.

16. The process of claim 15, wherein the crystalline pregabalin characterized by X-ray powder diffraction peaks at about 5.7, 15.4, 15.9, 17.2, 18.2, 18.5, 23.0, 25.2, and 25.6° 2θ±0.2° 2θ is heated to a temperature of at least about 120° C.

17. The process of claim 15, wherein the crystalline pregabalin characterized by X-ray powder diffraction peaks at about 5.7, 15.4, 15.9, 17.2, 18.2, 18.5, 23.0, 25.2, and 25.6° 2θ±0.2° 2θ is heated for at least about one hour.

18. A process for preparing a pharmaceutical formulation, comprising combining crystalline pregabalin characterized by X-ray powder diffraction peaks at about 5.8, 18.4, 19.2, 20.7, and 23.7° 2θ±0.2° 2θ with at least one pharmaceutically acceptable excipient.

19. A process for the manufacture of a pharmaceutical composition, comprising forming a pharmaceutical composition comprising crystalline pregabalin characterized by X-ray powder diffraction peaks at about 5.8, 18.4, 19.2, 20.7, and 23.7° 2θ±0.2° 2θ.

20. A process of preparing crystalline pregabalin characterized by X-ray powder diffraction peaks at about 5.7, 15.4, 17.2, 18.2, and 23.0° 2θ±0.2° 2θ, comprising exposing crystalline pregabalin characterized by X-ray powder diffraction peaks at about 5.8, 18.4, 19.2, 20.7, and 23.7° 2θ±0.2° 2θ to a relative humidity of about 80 to about 100 percent, at about room temperature for at least about a week.

21. The process of claim 20, wherein the relative humidity is of about 100 percent.

* * * * *